(12) United States Patent
Lee et al.

(10) Patent No.: US 7,502,105 B2
(45) Date of Patent: Mar. 10, 2009

(54) APPARATUS AND METHOD FOR PRODUCING A CALIBRATED RAMAN SPECTRUM

(75) Inventors: Yuan-Hsiang Lee, Winchester, MA (US); William Scott Sutherland, Haverhill, MA (US)

(73) Assignee: General Electric Company, Schenectady, NY (US)

( * ) Notice: Subject to any disclaimer, the term of this patent is extended or adjusted under 35 U.S.C. 154(b) by 363 days.

(21) Appl. No.: 10/941,565

(22) Filed: Sep. 15, 2004

(65) Prior Publication Data

US 2006/0055919 A1    Mar. 16, 2006

(51) Int. Cl.
*G01J 3/44* (2006.01)
(52) U.S. Cl. .................................. 356/301
(58) Field of Classification Search ............ 356/301
See application file for complete search history.

(56) References Cited

U.S. PATENT DOCUMENTS

| | | | |
|---|---|---|---|
| 5,020,909 A * | 6/1991 | Landa .................. | 356/300 |
| 5,404,218 A * | 4/1995 | Nave et al. ............ | 356/301 |
| 5,455,673 A | 10/1995 | Alsmeyer et al. ...... | 356/301 |
| 5,526,121 A * | 6/1996 | Sandifer et al. ....... | 356/418 |
| 5,850,623 A * | 12/1998 | Carman et al. ........ | 356/301 |
| 6,067,156 A * | 5/2000 | Slater et al. .......... | 356/301 |
| 6,141,095 A | 10/2000 | Allen et al. ........... | 356/301 |
| 6,281,971 B1 | 8/2001 | Allen et al. ........... | 356/301 |
| 6,621,574 B1 * | 9/2003 | Forney et al. ......... | 356/301 |
| 6,897,951 B2 | 5/2005 | Womble et al. | |

OTHER PUBLICATIONS

Favors, Ryan, New Raman External Standard for Absolute Intensity and Concentration Measurements, Chemistry Department, Purdue University West Lafayette, IN, United States, presented at Federation of Analytical Chemistry and Spectroscopy Societies (Oct. 2002).

* cited by examiner

*Primary Examiner*—Kara E Geisel
(74) *Attorney, Agent, or Firm*—Eugene Hyun, Esq.; Armstrong Teasdale LLP

(57) ABSTRACT

An apparatus for generating a Raman signal of a test sample is disclosed. The apparatus includes a first optical path, a second optical path, a first station, and a second station. The first optical path is adapted for coupling with a radiation source that produces a test beam at the first optical path. The first station is responsive to the test beam and is adapted to house a test standard. The second station is responsive to the test beam and is adapted to house the test sample. In response to the test beam, Raman radiation from the test standard and the test sample are combined and directed to the second optical path, which is adapted for coupling with a spectrometer and a detector for producing a Raman spectrum of the test sample.

31 Claims, 4 Drawing Sheets

APPARATUS AND METHOD FOR PRODUCING A CALIBRATED RAMAN SPECTRUM

BACKGROUND OF THE INVENTION

The present disclosure relates generally to an apparatus and method for producing a calibrated Raman spectrum, and particularly to an apparatus and method for producing a calibrated Raman spectrum using a test standard.

Spectroscopy refers to the study of energy or intensity as a function of wavelength in a beam of light or radiation. Raman spectroscopy refers to the study of the wavelength and intensity of inelastically scattered light from molecules, and an analytical technique that may be used for the analysis of covalently bound chemical substances found on surfaces or bulk materials. When a material is exposed to monochromatic radiation, a phenomenon known as Raman scattering results, which produces Raman spectra having frequencies that are characteristic of the exposed molecule and the various groups and bonds in the molecule. Raman scattered light is frequency-shifted with respect to the incident light excitation frequency by the energies of the molecular vibrations, and since the magnitude of the shift is independent of the excitation frequency, the resulting "Raman shift" is illustrative of an intrinsic property of the sample under test.

The Raman scattering effect is typically very weak and Raman spectrometers must be capable of separating the weak inelastically scattered light from the intense elastically scattered incident laser light. As a result, apparatus for producing Raman spectrum are sensitive to variations within the test apparatus itself, the test environment and the test sample.

In an effort to resolve some of the difficulties associated with Raman spectroscopy, several areas have been investigated for reducing system variability, including: the use of lasers having a high degree of wavelength stability; the use of lasers that generate infrared radiation so as to reduce fluorescence background problems; the use of radiation filtering devices to adequately reject the elastically scattered photons; the use of multi-dimensional charge coupled devices (CCD) for discerning extremely low levels of radiation; the use of a beam splitter to simultaneously irradiate a sample and a reference material in order to compensate for variabilities in the apparatus; the use of integral transform techniques for improved signal processing by removing undesirable frequency wanderings and intensities from the spectral data; the use of simultaneous data measurement of the excitation source and the Raman beam for precise arithmetic calculations; and, the use of beam monitoring at various points in the optical path for enabling higher precision and accuracy in the arithmetic calculations.

While existing apparatus for producing Raman spectrum may be suitable for their intended purpose, there still remains a need in the art for an apparatus and method for producing a calibrated Raman spectrum having a high degree of accuracy and repeatability.

BRIEF DESCRIPTION OF THE INVENTION

Embodiments of the invention include an apparatus for generating a Raman signal of a test sample, the apparatus having a first optical path, a second optical path, a first station, and a second station. The first optical path is adapted for coupling with a radiation source that produces a test beam at the first optical path. The first station is responsive to the test beam and is adapted to house a test standard. The second station is responsive to the test beam and is adapted to house the test sample. In response to the test beam, Raman radiation from the test standard and the test sample are combined and directed to the second optical path, which is adapted for coupling with a spectrometer and a detector for producing a Raman spectrum of the test sample.

Other embodiments of the invention include an apparatus for generating a Raman spectrum of a test sample, the apparatus having a radiation source for producing a test beam, a first station, a second station, a spectrometer, and a detector. The first station is responsive to the test beam and is adapted to house a test standard. The second station is responsive to the same test beam and is adapted to house the test sample. The spectrometer is disposed to receive and separate resultant Raman radiation from the test standard, the test sample, or any combination thereof. The detector is disposed to receive the separated Raman radiation and to produce a Raman spectrum thereof. Combined Raman radiation from the test standard and the test sample is used to generate a calibrated Raman spectrum of the test sample.

Further embodiments of the invention include a method of generating a Raman spectrum of a test sample using a radiation beam. Using a single radiation beam, a test standard, a test sample, or any combination thereof, is irradiated and spectral data from the resultant Raman radiation beam is obtained. A combined Raman spectrum of the test standard and the test sample is generated, and from the combined Raman spectrum a known Raman spectrum of the test standard is subtracted, thereby rendering a Raman spectrum of the test sample.

Additional embodiments of the invention include an apparatus for generating a Raman spectrum of a test sample as described above, in combination with a storage medium, readable by a processing circuit, storing instructions for execution by the processing circuit for carrying out the method described above. In addition, the processing circuit may compare the combined Raman spectrum with the Raman spectrum of the test standard, subtract from the combined Raman spectrum the Raman spectrum of the test standard thereby rendering a Raman spectrum of the test sample, and frequency shift the combined Raman spectrum, the rendered Raman spectrum of the test sample, or both, by an amount that would align the associated peaks of the combined Raman spectrum with those peaks of the known Raman spectrum of the test standard.

BRIEF DESCRIPTION OF THE DRAWINGS

Referring to the exemplary drawings wherein like elements are numbered alike in the accompanying Figures.

DETAILED DESCRIPTION OF THE INVENTION

An embodiment of the invention provides an apparatus for generating a Raman spectrum of a test sample, and more specifically for generating a calibrated Raman spectrum of the test sample. By using a test standard internal to the apparatus, alternatively referred to as an internal standard (IS), in combination with a test sample, alternatively referred to as a sample under test (SUT), a combination Raman spectrum may be generated using a radiation beam having a single beam path directed toward the IS and SUT. The combination Raman spectrum may then be analyzed and adjusted to produce a standard Raman spectrum of the SUT with system variation removed. As used herein, the term system variation refers to variations within the test apparatus, the test environment and the test sample.

Figure 1:
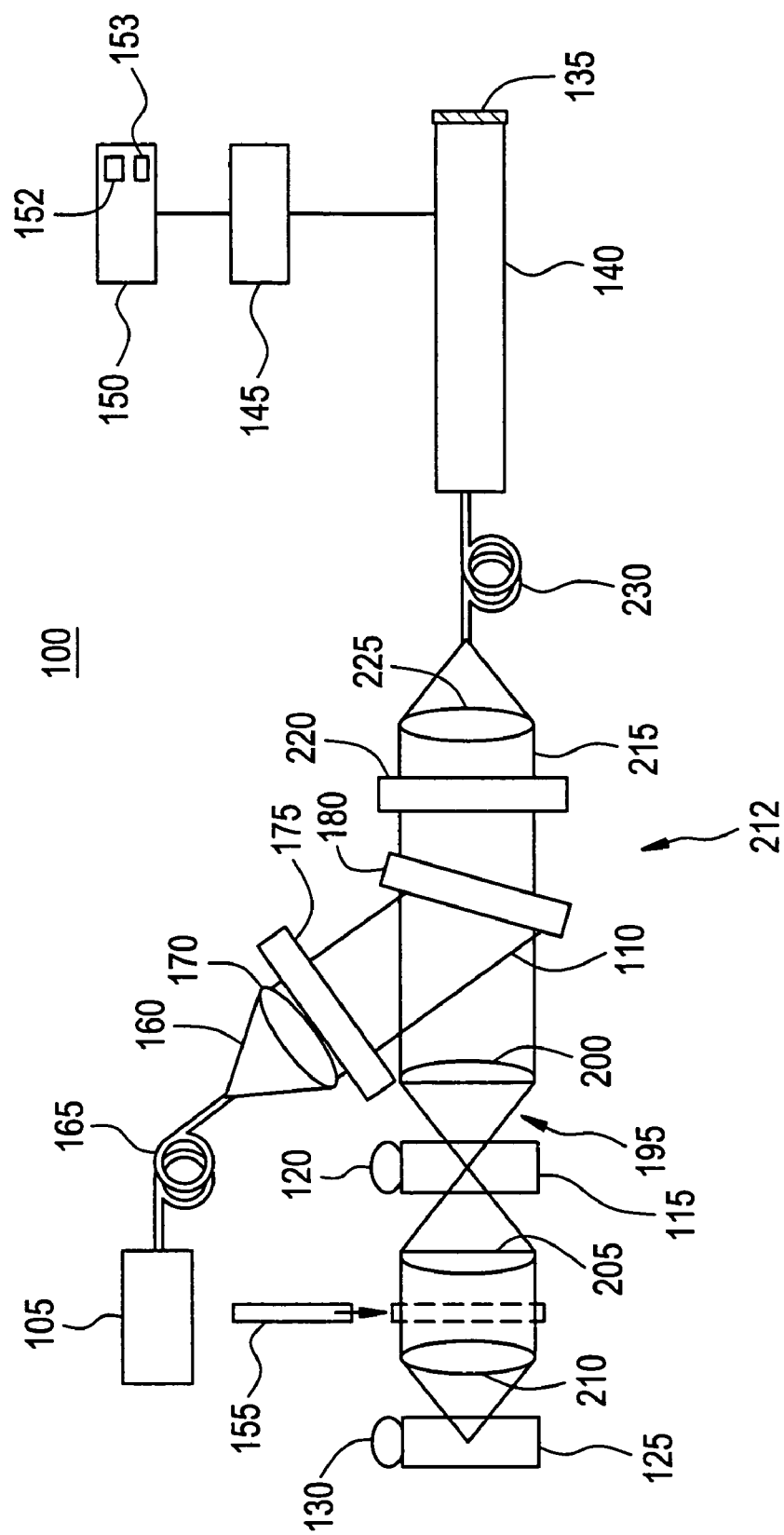
FIGS. 1-3 depict an exemplary apparatus in accordance with embodiments of the invention.

FIG. 1 is an exemplary embodiment of an apparatus 100 for generating a Raman spectrum of a test sample. In an embodiment, apparatus 100 includes a radiation source 105, such as a substantially monochromatic laser, for producing a test beam 110; a first station 115 adapted to house a test standard 120, a second station 125 adapted to house a test sample 130, and a spectrometer 140 containing a detector 135. As used herein, the term spectrometer is intended to be generally descriptive of a means to separate polychromatic light into its monochromatic components defined by a resolution or bandpass. Methods for separating the light may be based on filters, tunable filters, dispersion, separation, interferometry, or any other means suitable for obtaining monochromatic information. Light entering spectrometer 140 is separated, thereby illuminating detector 135 to produce a spectrum of the Raman radiation from test standard 120 and/or test sample 130. First and second stations 115, 125 are disposed such that each are responsive to the same test beam 110. In accordance with embodiments of the invention, the combined Raman radiation, generated by irradiating both test standard 120 and test sample 130 by the same test beam 110, is used to generate a calibrated Raman spectrum of test sample 130, which will be discussed in more detail later. While embodiments disclosed herein may refer to a spectrometer that spatially separates the Raman signal, it will be appreciated that the Raman signal may also be non-spatially separated by other techniques, such as by an interferometer, a tunable filter, or a Fourier Transform spectrometer, for example, and that the scope of the invention is not limited to only spectrometers that spatially separate the Raman signal.

Apparatus 100 may optionally include a device 155 for shuttering or switching, either mechanically or optically, the test beam 110 such that test beam 110 may or may not reach test sample 130. In an embodiment, device 155 is a mechanical shutter movably disposed between a first position, depicted in solid line, and a second position, depicted in dashed line, wherein the first position allows test beam 110 to reach test sample 130, and the second position prevents test beam 110 from reaching test sample 130. In an alternative embodiment, device 155 may be an optical shutter or an optical switch for causing the same result.

During the operation of laser 105, a laser beam 160 is directed through a waveguide 165 to lens 170, laser transmission filter 175, and laser rejection filter 180, resulting in test beam 110 being directed toward first 115 and second 125 stations via a single beam path 195. As used herein, the term waveguide refers to a means for guiding a light wave, and not necessarily to a specific structure of a specific waveguide, such as a fiber optic for example. While embodiments of the invention may employ fiber optics for waveguide 165, other embodiments may employ a laser 105 that is an integral part of the excitation/collection optical assembly (probe) 212, thereby eliminating the waveguide interface between the laser 105 and probe 212.

In the embodiment of FIG. 1, probe 212 is depicted generally as the excitation/collection optical assembly having lenses 170, 200, 205, 210, 225, and filters 175, 180, 220, however, embodiments of the invention are not so limited and may include fewer or additional optical elements, such as the absence of laser rejection filter 180 for example.

In response to shutter 155 being in the first position (open), test beam 110 passes through lens 200 to first station 115 where it irradiates test standard 120, then through lens 205 and lens 210 to second station 125 where it irradiates test sample 130. In an embodiment, test standard 120 is optically transparent to test beam 110, thereby permitting test beam 110 to pass through first station 115 and test standard 120 on its path toward second station 125 and test sample 130. As used herein, the phrase optically transparent test standard refers to a test standard that will permit at least a portion of the test beam to pass through the test standard, while another portion of the same test beam may be diffused by interaction with the test standard, thereby enabling both the test standard and the test sample to be exposed to the same instance of the test beam. The test standard may be fully or partially transparent or translucent, as long as a portion of the incident light is allowed to fall on the test sample. Accordingly, the invention disclosed herein is not limited to only a test standard capable of 100% transmittance. As used herein, the term transparent is intended to mean having the property of transmitting rays of light such that an object may be distinctly seen through the transparent article. Furthermore, the term translucent is intended to mean having the property of transmitting rays of light such that an object may not be clearly seen through the translucent article.

In response to shutter 155 being in the second position (closed), test beam 110 passes through lens 200 to first station 115 where it irradiates test standard 120, then only through lens 205 where it is radiated back by shutter 155. In an alternative embodiment, shutter 155 may be disposed between first station 115 and lens 205, so that the light is blocked before reaching lens 205. In another embodiment, shutter 155 is replaced by a fiber optic switch, as discussed previously. In response to only test standard, or both test standard and test sample, being irradiated, Raman radiation results therefrom. Whether shutter 155 is open or closed, the resulting Raman radiation beam 215 is directed through laser rejection filter 180, longpass filter 220, lens 225, and waveguide 230, where it is received at spectrometer 140 and detector 135.

In an embodiment, detector 135 is a two-dimensional charge-coupled-device (CCD) that converts the separated Raman radiation to produce a spectrum. In an alternative embodiment, the two-dimensional CCD detector 135 may be used in combination with a binning algorithm executed by a processing circuit, discussed later, for combining the charge from adjacent pixels in the two-dimensional CCD to produce an accumulated charge having an improved signal-to-noise ratio (SNR). By using a two-dimensional CCD detector 135 with binning, an effective one-dimensional CCD detector results. Alternatively, detector 135 may be a one-dimensional CCD detector.

Figure 2:
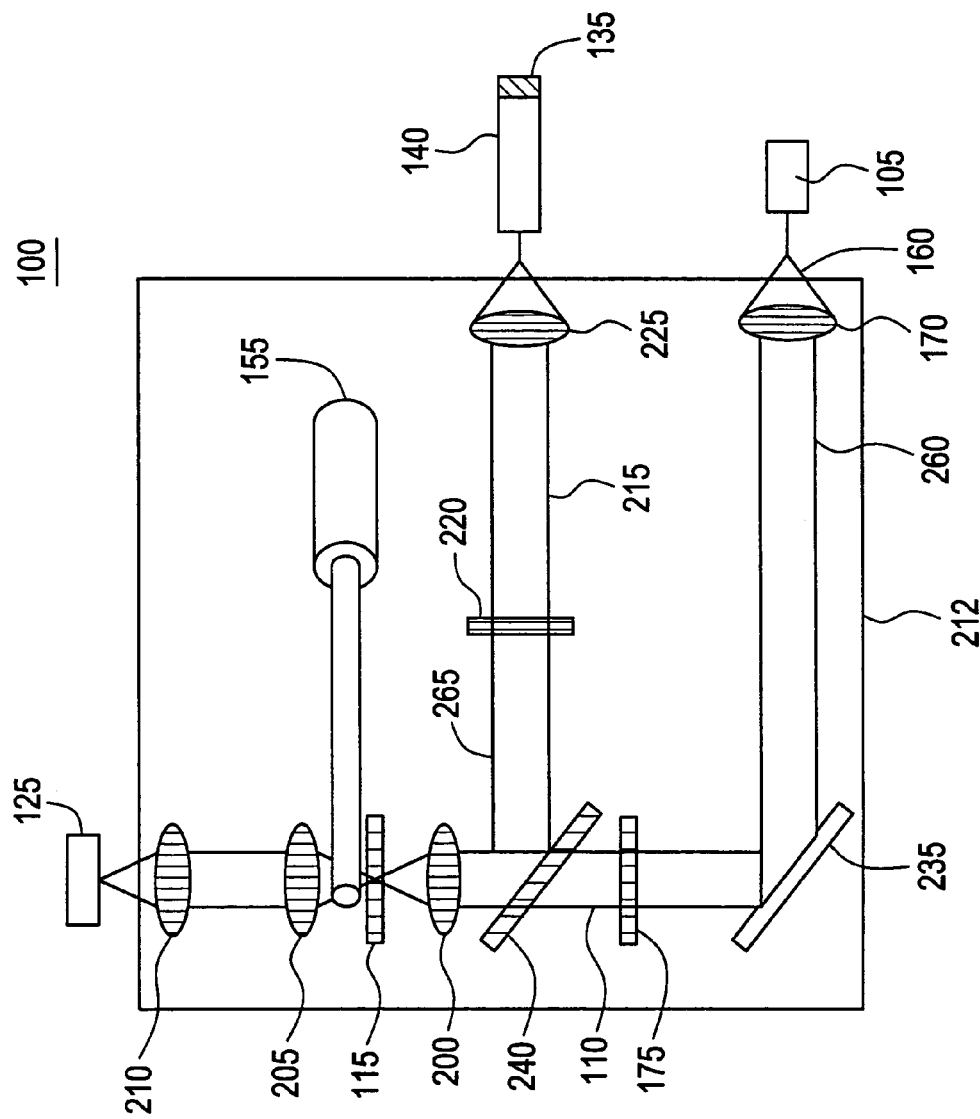

In an alternative embodiment, referring now to FIG. 2, apparatus 100 may have shuttering device 155 disposed to block light between first station 115 and lens 205, as discussed previously, and may position a laser 105 to direct a light beam toward a mirror 235 rather than toward the laser rejection filter 180 of FIG. 1. In the embodiment of FIG. 2, a beam splitter 240 may be employed. However, Raman radiation beams from test standard 120 at first station 115, and from test sample 130 at second station 125, are combined into a single beam path 215 directed toward spectrometer 140 and detector 135, which is similar to the single beam path 215 depicted in FIG. 1.

Figure 3:
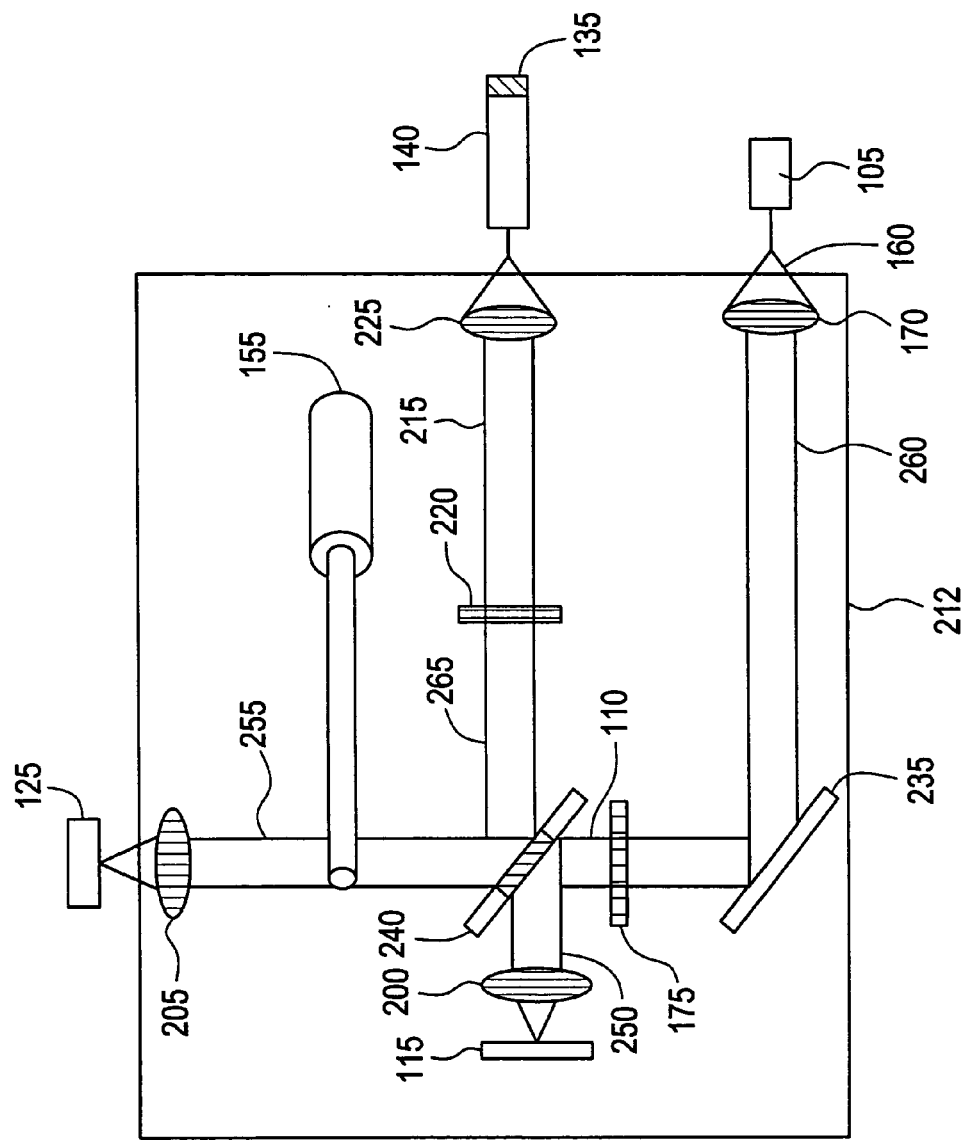

In a further alternative embodiment, referring now to FIG. 3, beam splitter 240 may be used in combination with a change in the placement of first station 115 and test standard 120. Here, beam splitter 240 directs a first beam 250 from laser 105 toward first station 115, and a second beam 255 from laser 105 toward second station 125. Raman radiation beams from test standard 120 and test sample 130 are combined into a single beam path 215, via beam splitter 240, and directed toward spectrometer 140 and detector 135. Single beam path 215 of FIG. 3 is similar to the single beam paths 215 of FIGS. 1 and 2. By employing a beam splitter 240 as depicted in FIG. 3, test standard 120 may be opaque rather than transparent. As used herein, the term opaque is intended to mean impervious to rays of light, not transparent.

As depicted in FIGS. 2 and 3, probe 212 may have a first optical path 260 adapted for coupling, via lens 170, with radiation source 105 that produces test beam 110, and a second optical path 265 adapted for coupling, via lens 225, with spectrometer 140 and detector 135. The Raman radiation from the test standard 120 and the test sample 130 are combined at the second optical path 265. While the probe 212 of FIG. 2 has a test beam 110 that is directed to first station 115 and second station 125 via a single beam path, such that the first and second stations are responsive to the same test beam, the probe 212 of FIG. 3 has a beam splitter 240 that is responsive to the test beam 110 and is productive of a first beam 250 directed to first station 115, and a second beam 255 directed to second station 125. However, regardless of whether test beam 110 is split or not, the resulting Raman radiation from test standard 120 and test sample 130 are combined into a single beam at the second optical path 265. Furthermore, either probe 212 of FIGS. 2 and 3 may include a means, such as a shutter 155 for example, for preventing the test beam 110 or the second beam 255 from reaching the test sample 130. In comparing the embodiments of FIGS. 1-3, it will be appreciated that the Raman radiation from test standard 120 and test sample 130 may be received at spectrometer 140 and detector 135 via a single beam path 215, thereby enabling the generation of a combined Raman spectrum by illumination of detector 135 from a single Raman beam.

Figure 4:
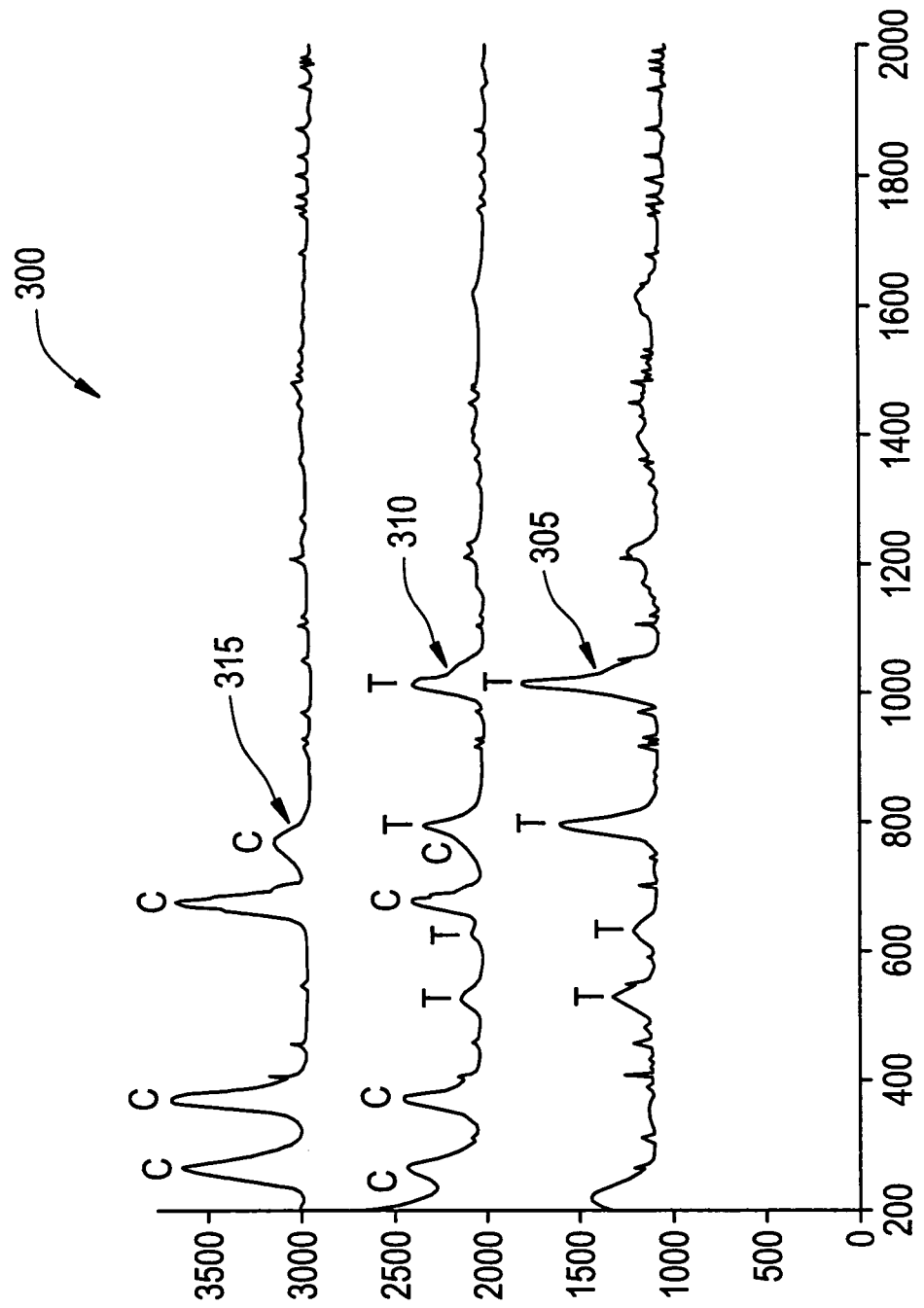
FIG. 4 depicts an illustration of exemplary Raman spectra using the apparatus of FIGS. 1-3.

In an embodiment, and referring now to FIGS. 1-4 collectively, apparatus 100 may also include a processing circuit 145 adapted, that is, having electronic circuitry configured and capable of executing instructions, to subtract the Raman spectrum 305 of test standard 120, such as toluene (T) for example, from the combined Raman spectrum 310 of test standard 120 and test sample 130, to generate a Raman spectrum 315 of test sample 130, such as chloroform (C) for example, best seen by now referring to FIG. 4. While only toluene and chloroform are disclosed as a test standard and test sample, respectively, it will be appreciated that any material capable of producing Raman radiation upon exposure to test beam 110 may be used in place thereof. In an embodiment, processing circuit 145 is further adapted to compare the peaks of combined Raman spectrum 310 to the peaks of test standard Raman spectrum 305, analyze the frequency difference between associated peaks, apply a frequency shift correction to combined Raman spectrum 310 thereby aligning the associated peaks, and then subtract test standard Raman spectrum 305 from combined Raman spectrum 310, thereby producing a calibrated test sample Raman spectrum 315. The aforementioned frequency shift correction may also, or alternatively, be applied to the spectral data collected at spectrometer 140 prior to the subtraction routine, or to test sample Raman spectrum 315 subsequent to the subtraction routine.

Apparatus 100 may further include a storage medium 150, readable by processing circuit 145, storing instructions for execution by processing circuit 145, for performing the data processing disclosed herein. Storage medium 150 may also be used for storing a library 152 of known Raman spectra.

Upon completion of the aforementioned comparison, analysis, shifting, and subtraction routines, processing circuit 145 may also be adapted to compare the Raman spectral peaks of the resulting test sample Raman spectrum 315 against the stored library of known Raman spectra, apply a best fit algorithm to match up the test sample Raman spectrum 315 with a suitable, if any, match in the library 152, and display the resulting match information, such as the compound name or letter designation, on user display 300. In the exemplary embodiment of FIG. 2, test sample Raman spectrum 315 is chloroform having letter designation (C), but may be any number of compounds having an associated Raman spectrum stored in library 152.

In view of the foregoing, apparatus 100 may generate a calibrated Raman spectrum 315 of test sample 130 in accordance with the following exemplary method. At the outset, an exemplary apparatus 100 is selected for its ability to irradiate test standard 120 and test sample 130 using the same radiation test beam 110, where test standard 120 and test sample 130 are arranged optically in series with each other. Using the single test beam 110, test standard 120 and/or test sample 130 are irradiated. Alternatively, a beam splitter 240 may be used where the resulting separate Raman beams are subsequently combined into a single Raman beam 215. In an embodiment, and using shutter 155, single test beam 110 is used to irradiate test standard 120, or test standard 120 in combination with test sample 130. From the resulting Raman radiation received at spectrometer 140 and detector 135, spectral data is collected and Raman spectrum generated therefrom, which may be a combined Raman spectrum 310 of test standard 120 and test sample 130, or a test standard Raman spectrum 305. From the combined Raman spectrum 310, a known Raman spectrum of the test standard 120 is subtracted, thereby rendering a Raman spectrum 315 of the test sample 130. The test standard Raman spectrum 305 may be generated by operating apparatus 100 with shutter 155 closed.

Prior to the aforementioned rendering of test sample Raman spectrum 315, the combined Raman spectrum 310 may be compared with the test standard Raman spectrum 305, and the combined Raman spectrum 310 frequency shifted by an amount that would align the associated peaks of combined Raman spectrum 310 with those peaks of known test standard Raman spectrum 305, thereby rendering a calibrated test sample Raman spectrum 315. In an alternative embodiment, test standard Raman spectrum 305 may be subtracted from combined Raman spectrum 310, and then the resulting test sample Raman spectrum 315 may be frequency shifted to produce a calibrated test sample Raman spectrum 315.

In a first exemplary method, test standard 120 and test sample 130 are irradiated using a single radiation test beam 110 to generate Raman radiation, with the resulting spectral data from spectrometer 140 and detector 135 producing a combined Raman spectrum 310. A test standard Raman spectrum 305 may be obtained by operating apparatus 100 to irradiate only test standard 120, which may be accomplished by closing device 155 and preventing the single radiation beam from irradiating test sample 130. The test standard Raman spectrum 305 is then used to render a calibrated Raman spectrum 315 of test sample 130 as discussed previously. In this manner, the calibrated Raman spectrum 315 of test sample 130 may be calibrated in real time, thereby removing real time variabilities in apparatus 100.

In a second exemplary method, apparatus 100 is used to irradiate only test standard 120 both before and after irradiating the combination of test standard 120 and test sample 130, thereby providing both a before and after test standard Raman spectrum 305 to further show that apparatus 100 is capable of providing a properly calibrated Raman spectrum of test sample 130.

In a third exemplary method, apparatus 100 is used to split the laser beam 160 to irradiate test standard 120 and test sample 130 by separate irradiating beams, and then to combine the two resulting Raman radiation beams into a single Raman beam directed towards the spectrometer 140 and detector 135 for subsequent analysis.

In view of the foregoing, apparatus 100 may be operated sequentially, first to obtain a Raman spectrum of test standard 120 (IS), and then to obtain a Raman spectrum of test sample 130 (SUT), with the resulting spectra being stored in memory 153 of storage medium 150 for subsequent data processing by processing circuit 145.

As disclosed, some embodiments of the invention may include some of the following advantages: use of an internal test standard to ensure proper calibration; the ability to use any number of different compounds as an internal test standard; the ability to correct for calibration drift on every scan of a test sample; the use of single beam irradiation for irradiating a plurality of objects with the same energy beam (that is, no beam splitter); the use of a single Raman beam for illuminating the detector (using a beam splitter); the use of single beam irradiation of the test standard in combination with the test sample for real time simultaneous spectral data collection of the combination; the ability to compare the Raman spectrum peaks of the test standard in the actual scan of the test sample to those both before and after to confirm proper and maintained calibration; and, the ability to utilize a self-calibration Raman probe for any kind of Raman spectroscopy including surface enhanced Raman spectroscopy (SERS).

Embodiments of the invention may also be embodied in the form of computer-implemented processes and apparatuses for practicing those processes. The present invention may also be embodied in the form of computer program code containing instructions embodied in tangible media, such as floppy diskettes, CD-ROMs, hard drives, USB (universal serial bus) drives, or any other computer readable storage medium, wherein, when the computer program code is loaded into and executed by a computer, the computer becomes an apparatus for practicing the invention. The present invention may also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein when the computer program code is loaded into and executed by a computer, the computer becomes an apparatus for practicing the invention. When implemented on a general-purpose microprocessor, the computer program code segments configure the microprocessor to create specific logic circuits. The technical effect of the executable instructions is to produce a calibrated Raman spectrum of a test sample from a combined Raman spectrum and a test standard Raman spectrum.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

What is claimed is:

1. An apparatus for generating a Raman signal of a test sample, the apparatus comprising:
    a radiation source that produces a test beam along a first optical path;
    a first station positioned on the first optical path and responsive to the test beam, the first station housing a test standard;
    a second station responsive to the test beam, the second station housing the test sample;
    a device configured to prevent the test beam from reaching the test sample; and
    a spectrometer comprising a detector for producing a Raman spectrum of the test sample, wherein the spectrometer is configured to receive a combined radiation beam comprising Raman radiation from the test standard and the test sample.

2. The apparatus of claim 1, further comprising:
    a test standard housed at the first station.

3. The apparatus of claim 1, wherein the second station is spaced a distance from the first station, and the test beam is directed towards the first station and the second station via a single beam path such that the first station and the second station are responsive to the test beam.

4. An apparatus for generating a Raman spectrum of a test sample, the apparatus comprising:
    a radiation source for producing a test beam;
    a first station responsive to the test beam, the first station housing a test standard;
    a second station responsive to the test beam, the second station housing the test sample;
    a device configured to prevent the test beam from reaching the test sample; and
    a detector configured disposed to receive separated Raman radiation and to produce a combined Raman spectrum of the test standard and the test sample, wherein the combined Raman spectrum is used to generate a calibrated Raman spectrum of the test sample.

5. The apparatus of claim 4, further comprising a processing circuit configured to;
    subtract a Raman spectrum of the test standard from the combined Raman spectrum; and
    generate a Raman spectrum of the test sample.

6. The apparatus of claim 5, wherein the processing circuit is further configured to apply a frequency shift to at least one of spectral data, the combined Raman spectrum, and the test sample Raman spectrum to produce the calibrated Raman spectrum of the test sample.

7. The apparatus of claim 6, wherein the processing circuit is further configured to compare the calibrated Raman spectrum of the test sample to a stored library of known spectrum.

8. The apparatus of claim 5, wherein the processing circuit is further configured to compare Raman spectral peaks from the Raman spectrum of the test standard with Raman spectral peaks from the combined Raman spectrum.

9. The apparatus of claim 4, wherein the test beam is directed to the first station and the second station via a single beam path.

10. The apparatus of claim 3, wherein the device comprises:
    a shutter movable between a first position and a second position, the first position allowing the test beam to reach the test sample, and the second position preventing the test beam from reaching the test sample.

11. The apparatus of claim 4, wherein:
the radiation source comprises a substantially monochromatic laser; and
the test standard is optically transparent.

12. The apparatus of claim 4, wherein:
the radiation source comprises a substantially monochromatic laser; and
the test standard is optically translucent.

13. The apparatus of claim 11, wherein the test beam passes through the test standard on a path toward the test sample.

14. The apparatus of claim 5, wherein the detector and the processing circuit render an effectively one-dimensional detector.

15. The apparatus of claim 14, wherein the detector comprises a two-dimensional detector and the processing circuit is further configured to bin the detected Raman radiation.

16. The apparatus of claim 4, wherein the detector is a one-dimensional detector.

17. The apparatus of claim 4, further comprising a spectrometer configured to receive and separate a resultant Raman radiation, wherein the resultant Raman radiation comprises at least a test standard Raman radiation and a test sample Raman radiation.

18. The apparatus of claim 17, wherein the test beam is directed to the first station and the second station via a beam splitter and separate beam paths, and wherein the resulting separate Raman radiation beams are combined into a single Raman beam directed toward the spectrometer.

19. The apparatus of claim 18, wherein:
the radiation source comprises a substantially monochromatic laser; and
the test standard is optically opaque.

20. A method of generating a Raman spectrum of a test sample using a radiation beam, said method comprising:
irradiating at least a test standard and the test sample using a single radiation beam;
selectively preventing the single radiation beam from irradiating the test sample:
generating a test standard Raman radiation based on the irradiated test standard;
generating a test sample Raman radiation based on the irradiated test sample;
combining at least the generated test standard Raman radiation and the generated test sample Raman radiation into a resultant Raman radiation beam;
obtaining spectral data from the resultant Raman radiation beam;
generating a combined Raman spectrum of the test standard and the test sample; and
subtracting from the combined Raman spectrum a known Raman spectrum of the test standard, thereby generating the Raman spectrum of the test sample.

21. The method of claim 20, wherein irradiating at least a test standard and the test sample using a single radiation beam further comprises irradiating a test standard and a test sample using the same radiation beam, the test standard and the test sample being arranged optically in series.

22. The method of claim 20, wherein irradiating at least a test standard and the test sample using a single radiation beam further comprises irradiating a test standard and a test sample using a split radiation beam.

23. The method of claim 20, further comprising:
generating a Raman spectrum of the test standard.

24. The method of claim 23, further comprising:
comparing the combined Raman spectrum with the Raman spectrum of the test standard; and
frequency shifting at least one of the combined Raman spectrum and the rendered Raman spectrum of the test sample by an amount to align associated peaks of the combined Raman spectrum with peaks of the known Raman spectrum of the test standard.

25. The method of claim 20, further comprising:
irradiating the test standard and the test sample using the single radiation beam, and obtaining combined spectral data therefrom;
irradiating only the test standard by preventing the single radiation beam from irradiating the test sample, and obtaining test standard spectral data therefrom;
using the combined spectral data and the test standard spectral data to generate the combined Raman spectrum and the test standard Raman spectrum; and
using the combined Raman spectrum and the test standard Raman spectrum to generate the Raman spectrum of the test sample.

26. The method of claim 25, further comprising:
frequency shifting at least one of the combined Raman spectrum and the test sample Raman spectrum by an amount to align associated peaks of the combined Raman spectrum with peaks of the test standard Raman spectrum to generate a calibrated Raman spectrum of the test sample.

27. The method of claim 26, further comprising:
subtracting the test standard Raman spectrum from the combined Raman spectrum to generate the calibrated Raman spectrum of the test sample.

28. The method of claim 20, further comprising:
irradiating only the test standard by preventing the single radiation beam from irradiating the test sample, and obtaining first test standard spectral data therefrom;
after obtaining the first test standard spectral data, irradiating the test standard and the test sample using the single radiation beam, and obtaining combined spectral data therefrom;
after obtaining the combined spectral data, irradiating only the test standard by preventing the single radiation beam from irradiating the test sample, and obtaining second test standard spectral data therefrom; and
using at least one of the first spectral data, the combined spectral data, and the second spectral data, to generate a calibrated Raman spectrum of the test sample.

29. An apparatus for generating a Raman spectrum of a test sample, the apparatus comprising:
a radiation source for producing a test beam;
a first station responsive to the test beam, the first station housing a test standard;
a second station responsive to the test beam, the second station housing the test sample;
a spectrometer disposed to receive and separate resultant Raman radiation from at least one of the test standard and the test sample;
a detector configured to receive the separated Raman radiation and to produce a Raman spectrum thereof; and
a storage medium, readable by a processing circuit, storing instructions for execution by the processing circuit for:
irradiating at least one of the test standard and the test sample;
obtaining spectral data from the resultant Raman radiation;
generating a combined Raman spectrum of the test standard and the test sample;
generating a Raman spectrum of the test standard;
comparing the combined Raman spectrum with the Raman spectrum of the test standard;

subtracting from the combined Raman spectrum the Raman spectrum of the test standard, thereby generating a Raman spectrum of the test sample; and frequency shifting at least one of the combined Raman spectrum and the generated Raman spectrum of the test sample by an amount to align associated peaks of the combined Raman spectrum with peaks of the Raman spectrum of the test standard.

30. An apparatus for generating a Raman signal of a test sample, the apparatus comprising:

a radiation source that produces a test beam along a first optical path;

a first station positioned on the first optical path and responsive to the test beam, the first station housing a test standard;

a second station responsive to the test beam, the second station housing the test sample;

a beam splitter responsive to the test beam to generate a first beam and a second beam, the first station being responsive to the first beam, and the second station being responsive to the second beam, wherein in response to the first and second beams, Raman radiation from the test standard and the test sample are combined into a combined radiation beam comprising Raman radiation from the test standard and Raman radiation from the test sample, the combined radiation beam directed along a second optical path; and a spectrometer comprising a detector for producing a Raman spectrum of the test sample, wherein the spectrometer is coupled to the second optical path and configured to receive the combined radiation beam.

31. The apparatus of claim 30, further comprising:

a device configured to prevent the second beam from reaching the test sample.

* * * * *